US00PP21963P3

(12) United States Plant Patent

Adam, Jr.

(10) Patent No.: US PP21,963 P3

(45) Date of Patent: May 31, 2011

(54) *TIARELLA* PLANT NAMED 'WISSAHICKON'

(50) Latin Name: *Tiarella cordifolia*
Varietal Denomination: Wissahickon

(75) Inventor: Sinclair A. Adam, Jr., Coatesville, PA (US)

(73) Assignee: Plants Nouveau—a division of Treadwell Palmer International, Inc., Baltimore, MD (US)

( * ) Notice: Subject to any disclaimer, the term of this patent is extended or adjusted under 35 U.S.C. 154(b) by 0 days.

(21) Appl. No.: 12/589,994

(22) Filed: Nov. 2, 2009

(65) Prior Publication Data

US 2011/0107486 P1 May 5, 2011

(51) Int. Cl.
*A01H 5/00* (2006.01)

(52) U.S. Cl. ..... Plt./486

(58) Field of Classification Search ..... Plt./486
See application file for complete search history.

*Primary Examiner* — June Hwu

(74) *Attorney, Agent, or Firm* — Penny J. Aguirre

(57) ABSTRACT

A new and distinct *Tiarella cordifolia* plant characterized by its glossy, deep green foliage and its white flowers that re-bloom throughout the summer.

2 Drawing Sheets

Botanical classification: *Tiarella cordifolia.*
Varietal denomination: 'Wissahickon'.

SUMMARY OF THE INVENTION

The new *Tiarella cordifolia* was selected during 2007 as a seedling from the garden at the Nursery of Sinclair A. Adam Jr. at Coatesville, Pa., U.S.A. The exact parentage of the new variety is unknown. It resulted from seedlings grown from open-pollinated plants of *Tiarella cordifolia*, and *Tiarella cordifolia* var. *collina*. Several hundred plants are grown for seed production, and some or all of these plants are likely included in the parentage of the new variety of the present invention.

The new variety has been carefully preserved and studied since the time of its discovery. Had such new variety not been discovered and preserved, it would have been lost to mankind.

It was found that the new *Tiarella cordifolia*, variety of the present invention exhibits the following combination of characteristics: (a) exhibits a compact mounding clump growth habit with substantial runners, (b) forms attractive white flowers on branched flower stalks, (c) forms lobed ovate green leaves having a glossy finish during the summer, deeper green in the late summer, and turn burgundy maroon with the progression of autumn, and winter. (d) is particularly well suited for growing as a distinctive ornamental ground cover, creating a dense stand in a season.

The new variety of the present invention can be readily distinguished from other previously known varieties of the species in view of the distinctive combination of characteristics discussed herein. The glossy green spring & summer, foliage and fall and winter color is considered to be particularly noteworthy.

The new variety well meets the needs of the horticultural industry and expands the choices of ornamental ground covers which fills in as a stand well. It performs well wherever a ground cover is desired, and is particularly well suited for use as a border planting, use in shaded areas, and for ecology and restoration casting open pollinated seedlings, and asexual runners.

The runners (stolons) and flower stems of clumps have been used to asexually propagate the new variety at Delhi, N.Y. (laboratory), and Coatesville, (breeder and Nursery) Pa., U.S.A. It has been found that the distinctive combination of characteristics of the new variety is firmly fixed and is reliably transmitted to succeeding generations. During observations to date, the new variety has been found to be readily amenable to such propagation.

The New variety 'Wissahickon' can be compared to 'Brandywine' (not patented), which differs from 'Wissahickon' in having fewer and shorter runners, white flowers with yellow anthers and pollen, and foliage suffused with maroon along the veins. 'Wissahickon' can also be compared to cultivars from the same breeding program, 'Octoraro' (U.S patent application Ser. No. 12/589,995), 'Delaware' (U.S. patent application Ser. No. 12/589,997), 'Susquehanna' (U.S. patent application Ser. No. 12/589,996), and 'Lehigh' (U.S. patent application Ser. No. 12/589,998). 'Octoraro' differs from 'Wissahickon' in having larger white flowers, foliage that in spring has maroon markings localized on the veins, and in having foliage that turns golden yellow with red veins in the fall. 'Delaware' differs from 'Wissahickon' in having red colored runners. 'Susquehanna' differs from 'Wissahickon' in having foliage that in spring has maroon markings localized on the veins only, and in having foliage that turns red with green margins in the fall.

The new variety has been named 'Wissahickon'.

DETAILED DESCRIPTION

Figure 1:
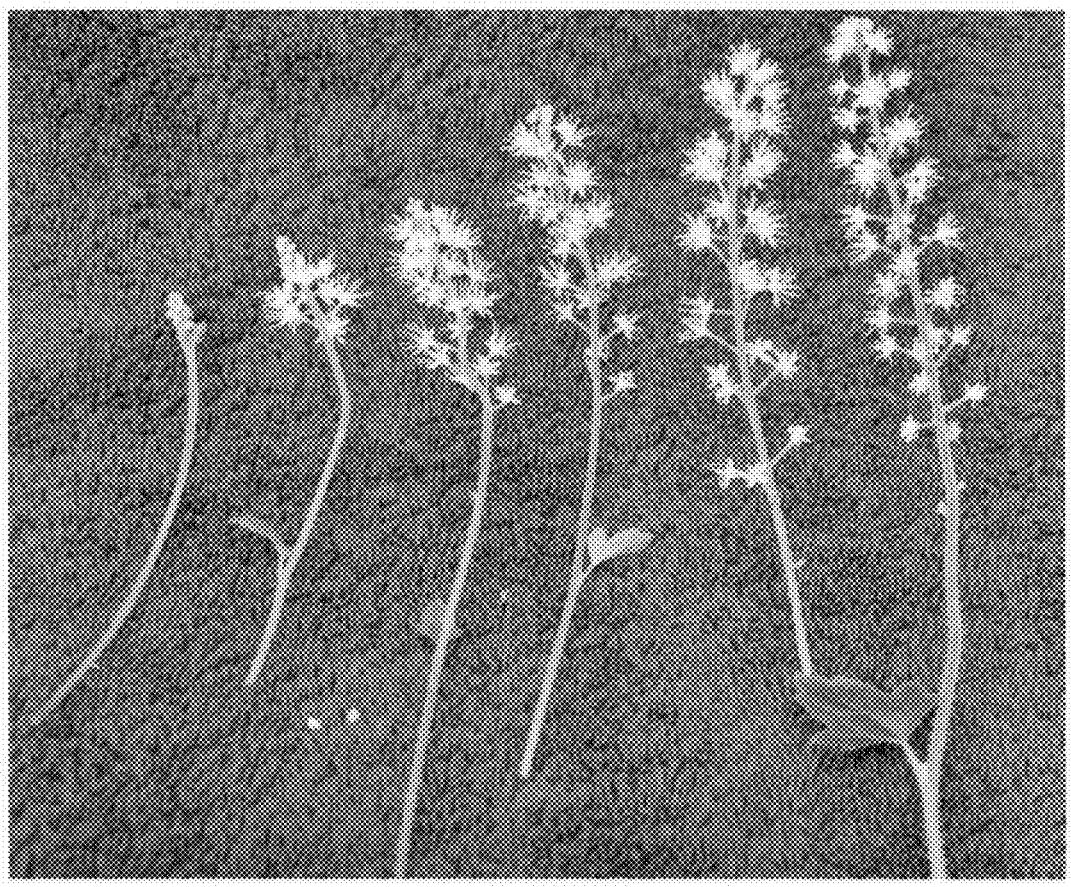
FIG. 1: shows a sequence of blooms on plants in Coatesville, Pa. in May.
Figure 2:
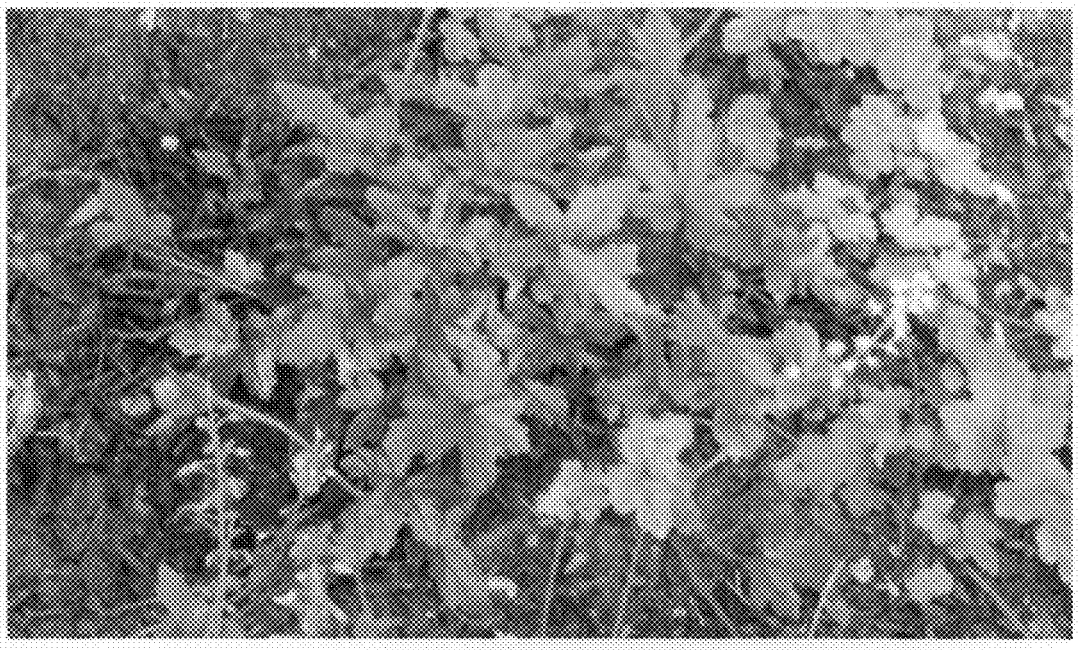
FIG. 2: shows two one year old plants in the ground in Collegeville, Pa. in August.
Figure 3:
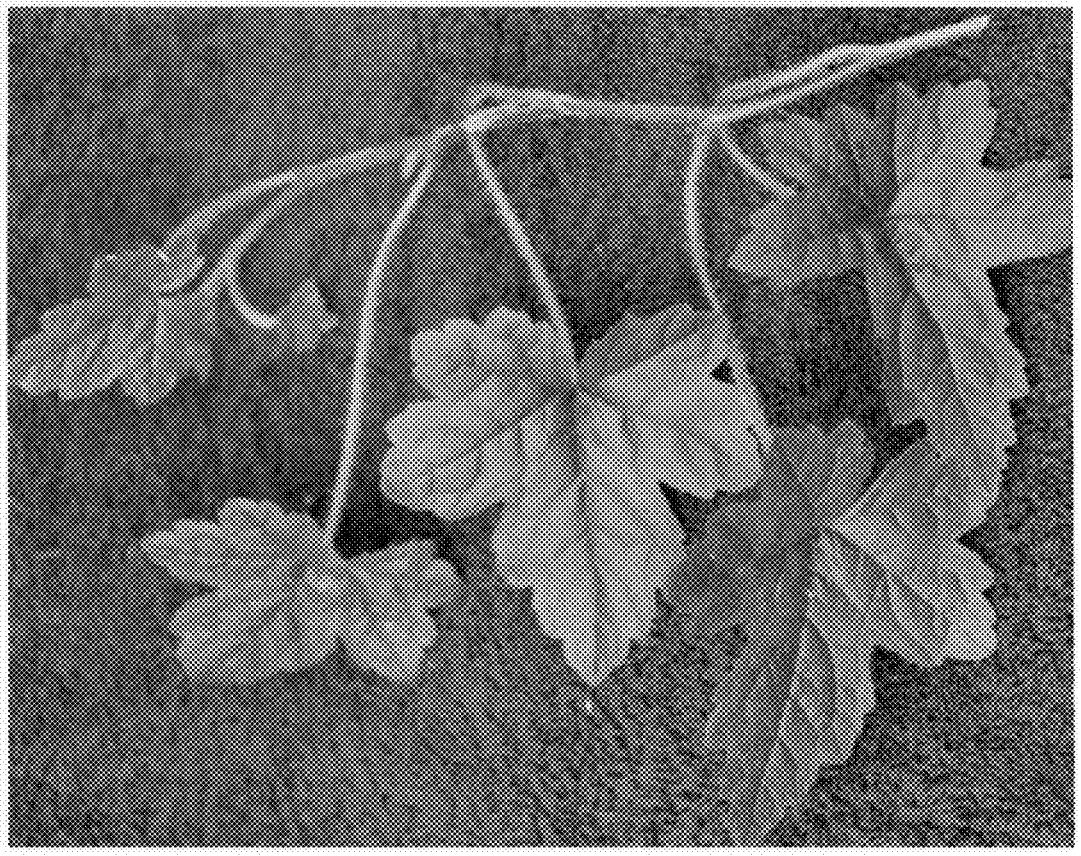
FIG. 3: shows a sequence of leaves from immature to mature in Coatesville, Pa. in May.

The following is a detailed description of the new variety that was obtained while observing plants being grown outdoors, and in the greenhouse during 2007-2008 at Coatesville, Pa., U.S.A. The plants were approximately two years of age and were being grown on their own roots. The chart used in the identification of color is The R.H.S. Colour Chart of The Royal Horticultural Society, London, England. More common color terms are to be accorded their ordinary dictionary significance.

Botanical classification: *Tiarella cordifolia* 'Wissahickon'.

Plant:

*Habit.*—Compact mounding clump, several runners.

*Type.*—Evergreen.

*Height.*—Approximately 12 to 18 cm without blooms, and approximately 30 to 35 cm with blooms.

*Width.*—Approximately 25 to 30 cm.

*Stolons.*—Slightly darker than Greyed-Purple Group 183C in color, surface is pubescent with hairs 2.5 to 3 mm in length, internode length 2.5 to 3 cm.

Foliage:

*Type.*—Simple.

*Shape.*—Ovate to broadly ovate, palmately five-lobed (seven-lobed as the leaf expands) with an elongated central lobe, and irregularly crenate margins on all lobes having mucronate teeth. Each tooth has a small point, which is relatively firm with a leaf vein extending to the end of the tip.

*Length.*—Approximately 7 to 10 cm.

*Width.*—Approximately 6 to 9 cm.

*Margins.*—Incised with dentation.

*Apex.*—The lobes are broadly obtuse to rounded and cuspidate.

*Base.*—Cordate.

*Texture.*—Upper surface; Slightly rugose with a velvet matte finish and pubescent with hairs 2 mm in length and 2 to 3 mm apart with greater density on margins, lower surface; pubescent with hairs 1 to 2 mm in length.

*Arrangement.*—Basal clump, with branched runners 6-8 in number, usually 30 to 40 cm in length.

*Venation.*—Palmately reticulate.

Young foliage: On the upper surface Yellow-Green Group 144A to 144B, and Greyed-Purple Group 187A at the center and along the main vein, and on the lower surface Yellow-Green Group 146B to 146C.

Adult foliage: On the upper surface Green Group 137B to 137D, and Brown Group 200B at the center and along the main vein, and on the lower surface Yellow-Green Group 146B to Greyed-Green Group 191A.

Fall foliage: Both the ventral leaf surface (upper) and the dorsal leaf surface (lower) are characterized by areas of light red and darker reddish-purple that are near and through the following colors: Red Group 49D and Red-Purple Group 62D in the lighter areas to Red Group 53D and Greyed-Purple Group 186B in the mid-tones to Greyed-Purple Group 187A and 187B in the darker areas. The dorsal leaf surface exhibits a slightly glossier appearance when compared to the more matte appearance of the ventral leaf surface that commonly is increased in expression in the autumn foliage.

*Winter foliage.*—Upper surface; Purple Group N77 in color, lower surface; Greyed-Purple Group 183D in color.

*Petiole.*—The length commonly varies from approximately 9 to 15 cm, and the diameter commonly is approximately 2 to 3 mm, surface texture is pubescent with hairs 0.5 to 2 mm in length, Greyed-Orange Group 177A in color.

Inflorescence:

*Type.*—Raceme and perfect (bisexual).

*Number.*—Approximately 30 to 40 blooms per raceme.

*Bearing.*—On a branched stalk commonly having a height of approximately 25 to 30 cm, with up to 2 to 3 short side branches. Side branches are 6 to 10 cm in length, bearing 15 to 20 blooms.

*Lastingness of inflorescence.*—About 3 weeks.

*Flower buds.*—Ellipsoid in shape, perigynous, 2 to 3 mm in depth and 2 mm in diameter, Red-Purple Group 62D in color.

*Calyx.*—Five-lobed, White Group N155A in color, about 7 mm in diameter.

*Petals.*—Five.

*Petal shape.*—Triangular.

*Stamens.*—Ten, 3 to 4 mm in length. Anthers Yellow-Orange Group 19 D.

*Pistil.*—One, 4 to 5 mm in length.

*Flower size.*—Approximately 6 to 9 mm in depth on average per floret.

*Color.*—On the dorsal surface White Group 155B and on the ventral surface White Group 155A.

*Fragrance.*—Slight and sweet.

*Pedicel.*—Approximately 6 to 9 mm in length, Red-Purple 61A in color.

Development:

*Vegetation.*—Clump-forming, with runners (stolons).

*Blooming.*—Abundantly when initially blooms during May/June and sporadically thereafter during the summer and fall.

*Resistance to disease.*—No susceptibility to diseases has been noted during observations to date.

*Hardiness.*—Has proven to grow well in U.S.D.A. Hardiness Zones No. 4 to 7.

*Propensity to form fruit/seeds.*—Approx 0.18 grams per (1 year old)plant (about 600 seeds).

Plants of the new 'Wissahickon' variety have not been observed under all possible environmental conditions to date. Accordingly, it is possible that the phenotype expression may vary somewhat with changes in light intensity and duration, cultural practices, and other environmental conditions.

I claim:

1. A new and distinct *Tiarella* plant as herein illustrated and described.

* * * * *